United States Patent [19]
Marshall

[11] 4,027,658
[45] June 7, 1977

[54] INSTRUMENT FOR TAKING SAMPLES

[76] Inventor: Manly Ernest Marshall, 1824 Grove Ave., Richmond, Va. 23220

[22] Filed: Dec. 1, 1975

[21] Appl. No.: 636,570

[52] U.S. Cl. .............................. 128/2 W; 128/304
[51] Int. Cl.² ...................................... A61B 10/00
[58] Field of Search ........... 128/2 W, 2 B, 304, 311

[56] References Cited
UNITED STATES PATENTS

| | | | |
|---|---|---|---|
| 2,514,665 | 7/1950 | Myller | 128/2 B |
| 2,835,246 | 5/1958 | Boettger | 128/2 W |
| 2,955,591 | 10/1960 | MacLean | 128/2 B |
| 3,308,825 | 3/1967 | Cruse | 128/2 F X |
| 3,388,043 | 6/1968 | Ingvorsen | 128/2 W |
| 3,815,580 | 6/1974 | Oster | 128/2 W |
| 3,828,765 | 8/1974 | McDonald | 128/2 B |
| 3,838,681 | 10/1974 | Dalton | 128/2 B |

*Primary Examiner*—Kyle L. Howell
*Attorney, Agent, or Firm*—Griffin, Branigan and Butler

[57] ABSTRACT

An instrument for taking samples from minute channels in the human body comprises a stem, a head and a handle integrally formed of plastic material. The stem is flexible and may be easily cut. The head has a rounded end and defines grooves therein for accepting samples.

9 Claims, 4 Drawing Figures

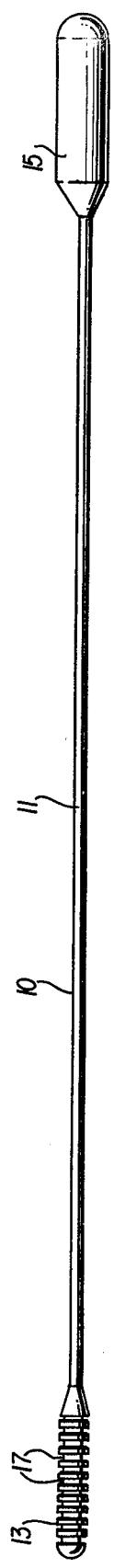
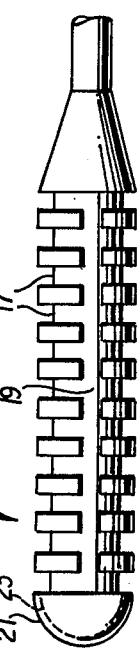
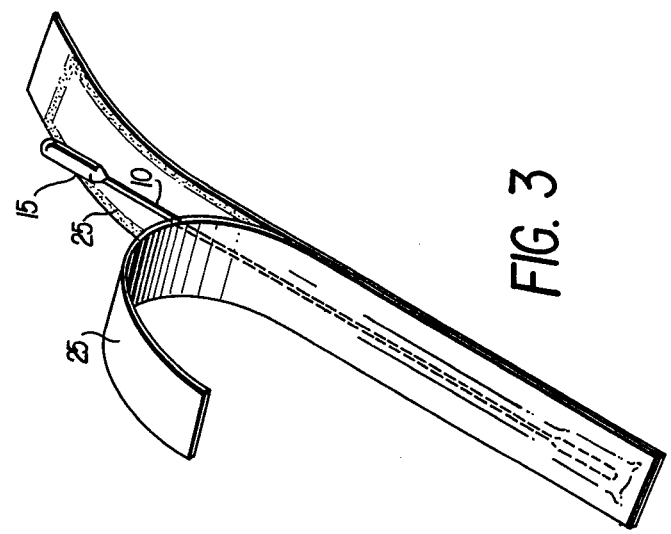
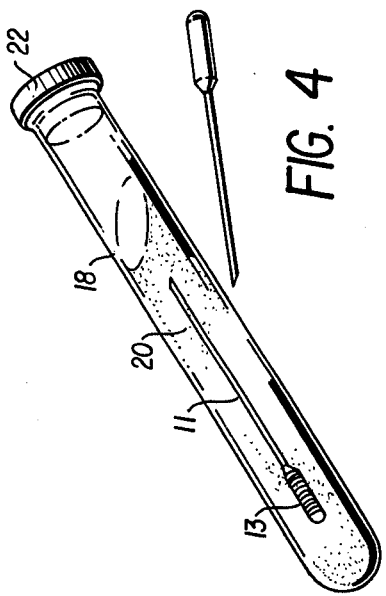

4,027,658

INSTRUMENT FOR TAKING SAMPLES

BACKGROUND OF THE INVENTION

This invention relates to instruments for taking samples and has particular use as a medical instrument for taking cultures from minute channels in the human body.

In taking biological samples, swabs comprising stems having absorbent material affixed thereto at one end have long been used. However, absorbent materials, such as cotton is generally too wide for convenient use in minute channels in the body, such as a urethra. Such materials progress along a urethra only with difficulty, and cause significant discomfort and pain to a patient.

To avoid the problems of cotton swabs, physicians have relied on bacteriological wires with or without loops formed at the ends. Such wires are non-disposable and thus require sterilization before each use. The use of a straight wire presents a significant risk of puncturing the urethra with a sharp, unguarded tip of the wire. A puncture aids the spread of bacteria and fungi, and may result in the formation of a suburethral abscess or stricture of the urethra. The risk of puncture is increased by the inflexibility of the wire. In addition to the dangers of bacteriological wires, the sharp unguarded tip on the inflexible wire causes pain to the patient. Finally, because of the small diameter of the wire and the lack of a specialized tip, very small samples are obtained for culture and/or staining.

It is therefore an object of this invention to provide an instrument for taking samples from minute channels in the human body without causing undue pain or physical damage to a patient. It is a further object of this invention to provide an instrument for taking samples having a minute, specialized tip.

It is also an object of this invention to provide an instrument for taking samples which is sufficiently flexible for following extended channels.

It is a further object of this invention to provide an instrument for taking samples which is inexpensive and thus disposable to eliminate the requirement for sterilization of the instrument after use.

After taking a sample, a physician generally prefers to immediately streak the culture across Thayer-Martin agar plates. The agar may be contained in transgrow bottles; hence, a stem of several inches facilitates the streaking process. And a stem of several inches is generally required in the taking of a sample from the urethra or like channel.

When an agar plate is not immediately available, a sampling instrument must be placed in a small vial of thioglycollate transfer medium. A stem sufficiently long for taking a sample and streaking the sample in a transgrow bottle is generally too long to be carried in the usual transfer vial. To overcome this problem, the use of detachable handles on short stems has been suggested. An example of such a device is found in Boettger (U.S. Pat. No. 2,835,246) However, in Boettger, the handle is too wide to be inserted into many body channels. Hence, the problem of providing a long stem for insertion into a body channel which is compatible with the use of small transfer vials still exists. It is a further object of this invention to provide an instrument for taking samples which solves this problem.

SUMMARY OF THE INVENTION

In accordance with principles of the invention an instrument for taking samples comprises a stem, a head, and a handle integrally formed of plastic material. The stem is of a small diameter such that it is relatively flexible. The head and handle are of larger diameters such that they are relatively inflexible. The head has grooves formed therein for accepting samples.

BRIEF DESCRIPTION OF THE DRAWINGS

The foregoing and other objects, features, and advantages of the invention will be apparent from the following more particular description of preferred embodiments as illustrated in the accompanying drawings in which like reference characters refer to the same parts throughout the various views. The drawings are not necessarily to scale, emphasis instead being placed upon illustrating principles of the invention.

FIG. 1 is a side view of an instrument embodying the invention;

FIG. 2 is an enlarged side view of the sampling head of the instrument of FIG. 1;

FIG. 3 is a schematic pictorial illustration of the instrument of FIG. 1 in a disposable package; and FIG. 4 is a sectional, exploded view of the FIG. 1 instrument cut and in a vial.

DESCRIPTION OF A PREFERRED EMBODIMENT

An instrument for taking samples 10, shown in FIG. 1, comprises a stem 11, a sampling head 13, and a handle 15. The stem, head, and handle are integrally formed of solid nylon, one of the many plastic polymers, or any other suitable plastic material. The head is of a diameter less than 6mm and preferrably of about 3 mm. which is significantly smaller than the average diameter of the male or female urethra of about 6 mm. The stem 11 has a diameter of 1 mm. The small diameter renders the stem very flexible and thus able to bend with the urethra or like channel. The lesser diameter also ensures that there is very little resistance to insertion of the head into the urethra. Because of the small diameter of the stem, it is not easily gripped by a physician, hence the necessity of the handle 15. The handle 15 is of a diameter such that the physician may easily grip the sampling instrument during insertion. Preferrably, the handle diameter is about 5mm.

For use in the urethra, the overall length of the instrument should be about 15cm. The head 13 is preferrably about 1cm long in order to collect a generous sample and the handle 15 may be between 2 and 3 cm long.

The head 13 overcomes the various problems presented by a bacteriological wire. That is, lateral grooves 17 and longitudinal grooves 19 (FIG. 2) are provided in the head 13 for accepting generous quantities of a sample. These grooves are about 0.5mm deep. The tip of the head 13 is rounded at 21, thereby preventing any undue pain or physical damage to a patient. An additional end groove 23 is provided in the curved surface 21.

FIG. 3 depicts a packaging for the disposeable sampling instrument 10. Two sheets 25 are adhesively joined to provide a sterile pocket for the instrument 10. FIG. 3 shows the package in a partially open state. Once the sheets 25 are pulled back partially, the handle 15 may be grasped to pull the instrument out of the package.

In use, the head and stem of the instrument are inserted into the urethra, the instrument at all times being grasped only by the handle 15. The instrument can be moved back and forth and rotated against the urethral mucosa in order to gather material into the grooves 17 and 19 of the head 13. The stem being flexible, it bends with the uretha. After the sample is collected, the head is gently rolled across the surface of a microscope slide or Thayer-Martin plate. The sampling instrument 10 may then be immediately disposed of.

When a slide or Thayer-Martin plate is not immediately available, at least the head and part of the stem must be inserted into a vial 18 of thioglycollate medium. Accordingly, the head 13 is plunged into a medium 20 (FIG. 4) and the stem 11 is cut with scissors (as shown in FIG. 4) to allow a cap 22 to be placed on the vial 18. Once the sample has been taken to a laboratory, the instrument may be removed from the vial using forceps and rolled over a Thayer-Martin medium.

It will be appreciated that the above described device has many advantages. Firstly, the device is disposable after removal from a sterile package; hence no sterilization of the device after each use is required. Also, the device may be manufactured to have a head diameter sufficiently small so as not to cause dilation of the urethra, thereby eliminating discomfort to patients. Further, the risk of puncturing urethras is virtually eliminated due to the flexiblity of the stem and the rounded head. Also, a large sample of urethral material is collected by the grooves in the head.

While the invention has been particularly shown and described with reference to a preferred embodiment thereof, it will be understood by those skilled in the art that various alterations in form and detail may be made therein without departing from the spirit and scope of the invention. For example, any format of grooves is possible; in fact, the grooves may be completely at random.

The embodiments of the invention in which an exclusive property or privilege is claimed are defined as follows:

1. An instrument for taking samples comprising a stem, a head, and a handle wherein
   said stem, head, and handle are formed of a single polymer material in a solid unitary construction, said head and handle being formed at opposed ends of said stem,
   said stem is of a substantially constant diameter,
   said stem is of a diameter such that it is flexible,
   said head and handle are of diameters larger than said stem such that they are relatively inflexible,
   said head is cylindrical and of a substantially constant diameter of less than 6 millimeters, and
   said head has grooves formed therein for accepting samples.

2. The instrument for taking samples of claim 1 wherein the ratio of head diameter to stem diameter is approximately 3 to 1.

3. The instrument for taking samples of claim 2 wherein said head diameter is about three millimeters.

4. The instrument for taking samples of claim 1 wherein the end of said head is rounded.

5. The instrument for taking samples of claim 1 wherein the diameter of said head is about 3 millimeters.

6. The instrument for taking samples of claim 5 wherein the depth of said grooves is about 0.5 millimeters.

7. The instrument for taking samples of claim 5 wherein the length of said head is about 1 centimeter.

8. The instrument for taking samples of claim 1 wherein said grooves include a plurality of circumferential grooves and longitudinal grooves.

9. The instrument for taking samples of claim 8 wherein the depth of said grooves is about 0.5 millimeters.

* * * * *